(12) United States Patent
Smilde et al.

(10) Patent No.: US 10,162,271 B2
(45) Date of Patent: Dec. 25, 2018

(54) METROLOGY METHOD AND APPARATUS, SUBSTRATE, LITHOGRAPHIC SYSTEM AND DEVICE MANUFACTURING METHOD

(71) Applicant: ASML Netherlands B.V., Veldhoven (NL)

(72) Inventors: Hendrik Jan Hidde Smilde, Veldhoven (NL); Bastiaan Onne Fagginger Auer, Utrecht (NL); Davit Harutyunyan, Eindhoven (NL); Patrick Warnaar, Tilburg (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/115,229

(22) PCT Filed: Dec. 30, 2014

(86) PCT No.: PCT/EP2014/079443
§ 371 (c)(1),
(2) Date: Jul. 28, 2016

(87) PCT Pub. No.: WO2015/113724
PCT Pub. Date: Aug. 6, 2015

(65) Prior Publication Data
US 2016/0334715 A1    Nov. 17, 2016

(30) Foreign Application Priority Data
Feb. 3, 2014  (EP) ................................. 14153611

(51) Int. Cl.
*G01B 11/00* (2006.01)
*G01B 11/04* (2006.01)
(Continued)

(52) U.S. Cl.
CPC ........... *G03F 7/70625* (2013.01); *G01B 9/04* (2013.01); *G03F 7/70633* (2013.01);
(Continued)

(58) Field of Classification Search
CPC .................. G01B 2210/56; G01B 9/04; G01N 2021/8822; G03F 7/70616; G03F 7/70625;
(Continued)

(56) References Cited

U.S. PATENT DOCUMENTS 7,113,256 B2  9/2006  Butler et al.
7,375,810 B2  5/2008  Nikoonahad et al.
(Continued)

FOREIGN PATENT DOCUMENTS

CN  1658073    8/2005
CN  103201682  7/2013
(Continued)

OTHER PUBLICATIONS

Chinese Office Action dated May 18, 2017 in corresponding Chinese Patent Application No. 201480077541.2 (17 pages).
(Continued)

*Primary Examiner* — Colin Kreutzer
(74) *Attorney, Agent, or Firm* — Pillsbury winthrop Shaw Pittman LLP

(57) ABSTRACT

In a dark-field metrology method using a small target, a characteristic of an image of the target, obtained using a single diffraction order, is determined by fitting a combination fit function to the measured image. The combination fit function includes terms selected to represent aspects of the physical sensor and the target. Some coefficients of the combination fit function are determined based on parameters of the measurement process and/or target. In an embodiment the combination fit function includes jinc functions repre-
(Continued)

senting the point spread function of a pupil stop in the imaging system.

20 Claims, 8 Drawing Sheets

(51) Int. Cl.
| | | |
|---|---|---|
| G03B 27/32 | (2006.01) | |
| G03B 27/74 | (2006.01) | |
| G03F 7/20 | (2006.01) | |
| G03F 9/00 | (2006.01) | |
| G01B 9/04 | (2006.01) | |
| G01N 21/88 | (2006.01) | |

(52) U.S. Cl.
CPC ........ *G03F 7/70641* (2013.01); *G03F 9/7092* (2013.01); *G01B 2210/56* (2013.01); *G01N 2021/8822* (2013.01)

(58) Field of Classification Search
CPC ............ G03F 7/70633; G03F 7/70641; G03F 9/7007; G03F 9/7092; H01L 22/12
USPC .............. 355/67, 68, 77; 356/399–401, 636; 430/22
See application file for complete search history.

(56) References Cited

U.S. PATENT DOCUMENTS

| | | |
|---|---|---|
| 7,508,976 B1 | 3/2009 | Yang et al. |
| 8,339,595 B2 | 12/2012 | Den Boef |
| 8,411,287 B2 | 4/2013 | Smilde et al. |
| 9,081,303 B2 | 7/2015 | Cramer et al. |
| 9,110,385 B2 | 8/2015 | Den Boef |
| 9,134,256 B2 | 9/2015 | Smilde et al. |
| 9,140,998 B2 | 9/2015 | Smilde et al. |
| 9,261,772 B2 | 2/2016 | Quintanilha |
| 2006/0098199 A1 | 5/2006 | Nikoonahad et al. |
| 2009/0106279 A1 | 4/2009 | Bae |
| 2010/0328655 A1 | 12/2010 | Den Boef |
| 2011/0027704 A1 | 2/2011 | Cramer et al. |
| 2011/0043791 A1 | 2/2011 | Smilde et al. |
| 2011/0069292 A1 | 3/2011 | Den Boef |
| 2012/0044470 A1 | 2/2012 | Smilde et al. |
| 2012/0123581 A1 | 5/2012 | Smilde et al. |
| 2012/0123748 A1 | 5/2012 | Aben et al. |
| 2012/0177282 A1* | 7/2012 | Chen .................... G06T 5/002 382/145 |
| 2013/0258310 A1 | 10/2013 | Smilde et al. |
| 2013/0271740 A1 | 10/2013 | Quintanilha |
| 2015/0138523 A1 | 5/2015 | Jak et al. |

FOREIGN PATENT DOCUMENTS

| | | |
|---|---|---|
| JP | 2005-520353 | 7/2005 |
| JP | 2013-501355 | 1/2013 |
| JP | 2013-534044 | 8/2013 |
| WO | 2009/078708 | 6/2009 |
| WO | 2009/106279 | 9/2009 |
| WO | 2013/143814 | 10/2013 |
| WO | 2013/178422 | 12/2013 |

OTHER PUBLICATIONS

Japanese Office Action dated Aug. 1, 2017 in corresponding Japanese Patent Application No. 2016-549489 (11 pages).
International Search Report and Written Opinion dated May 18, 2015 in corresponding International Patent Application No. PCT/EP2014/079443.
Korean Office Action dated Dec. 15, 2017 in corresponding Korean Patent Application No. 10-2016-7024348.
Chinese Office Action dated Jan. 19, 2018 in corresponding Chinese Patent Application No. 201480077541.2.
Chinese Office Action issued in corresponding Chinese Patent Application No. 201480077541.2, dated Jul. 23, 2018.

\* cited by examiner

METROLOGY METHOD AND APPARATUS, SUBSTRATE, LITHOGRAPHIC SYSTEM AND DEVICE MANUFACTURING METHOD

CROSS-REFERENCE TO RELATED APPLICATIONS

This application is the U.S. national phase entry of PCT patent application Ser. No. PCT/EP2014/079443, which was filed on Dec. 30, 2014, which claims the benefit of priority of EP patent application Ser. No. 14153611, which was filed on Feb. 3, 2014 and which is incorporated herein in its entirety by reference.

BACKGROUND

Field of the Invention

The present invention relates to methods and apparatus for metrology usable, for example, in the manufacture of devices by lithographic techniques and to methods of manufacturing devices using lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined Determination of the property of interest may be performed by various techniques: e.g., reconstruction of the target structure by iterative approaches such as rigorous coupled wave analysis or finite element methods; library searches; and principal component analysis.

The targets used by conventional scatterometers are relatively large, e.g., 40 µm by 40 µm, gratings and the measurement beam generates a spot that is smaller than the grating (i.e., the grating is underfilled). This simplifies mathematical reconstruction of the target as it can be regarded as infinite. However, in order to reduce the size of the targets, e.g., to 10 µm by 10 µm or less, e.g., so they can be positioned in amongst product features, rather than in the scribe lane, metrology has been proposed in which the grating is made smaller than the measurement spot (i.e., the grating is overfilled). Typically such targets are measured using dark field scatterometry in which the zeroth order of diffraction (corresponding to a specular reflection) is blocked, and only higher orders processed. Examples of dark field metrology can be found in international patent applications WO 2009/078708 and WO 2009/106279 which documents are hereby incorporated by reference in their entirety. Further developments of the technique have been described in published patent publications US20110027704A, US20110043791A, US20120044470, US2012/0123581, US 2013/0271740 A1 and WO2013143814 A1. The contents of all these applications are also incorporated herein by reference.

Diffraction-based overlay using dark-field detection of the diffraction orders enables overlay measurements on smaller targets. These targets can be smaller than the illumination spot and may be surrounded by product structures on a wafer. Multiple gratings can be measured in one image, using a composite grating target.

In the known metrology technique, overlay measurement results are obtained by measuring the target twice under certain conditions, while either rotating the target or changing the illumination mode or imaging mode to obtain separately the $-1^{st}$ and the $+1^{st}$ diffraction order intensities. Comparing these intensities for a given grating provides a measurement of asymmetry in the grating, and asymmetry in an overlay grating can be used as an indicator of overlay error.

Because of the reduced size of the individual gratings in a composite grating target, edge effects (fringes) in the dark-field image become significant, and there can be crosstalk between the images of different gratings within the target. To address this issue, US20110027704A mentioned above teaches to select only a central portion of the image of each grating as a 'region of interest' (ROI). Only pixel values within the ROI are used to calculate asymmetry and overlay. As one considers ever smaller targets, however, the size of ROI that can be defined to be free of edge effects reduces to ever smaller numbers of pixels. Consequently the measurements are inherently more noisy, for a given acquisition time. Moreover, any variation in positioning the ROI becomes a significant source of error in the measured asymmetry.

SUMMARY OF THE INVENTION

It is desirable to provide a technique for overlay metrology which maintains the benefits of using small gratings in composite target structures, in which accuracy can be improved over prior published techniques.

A first aspect of the invention provides a method of measuring a property of a lithographic process, using a target structure that has been formed by said lithographic process on a substrate, the method comprising the steps of: forming an image of the target structure using an imaging system that selects a predetermined portion of radiation diffracted by the target structure under predetermined illumination conditions; measuring the image of the target structure identifying one or more regions of interest in the measured image; and determining a value of at least one coefficient of a combination fit function using pixel values of the one or more regions of interest; wherein the value of the coefficient is indicative of the property.

A second aspect of the invention provides an inspection apparatus for measuring a property of a lithographic process using a target structure that has been formed by said lithographic process on a substrate, the apparatus comprising: a support for the substrate having said target structure formed thereon; an illumination system for illuminating the composite target structure under predetermined illumination conditions; an imaging system for forming an image of the composite target structure using a predetermined portion of radiation diffracted by the component target structures under said illumination conditions; a measuring system for measuring the image; a processor arranged to identify one or more regions of interest in the detected image and to determine a value of at least one coefficient of a combination fit function using pixel values of the one or more regions of interest; wherein the value of the coefficient is indicative of the property.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying drawings in which.

DETAILED DESCRIPTION OF EXEMPLARY EMBODIMENTS

Before describing embodiments of the invention in detail, it is instructive to present an example environment in which embodiments of the present invention may be implemented.

Figure 1:
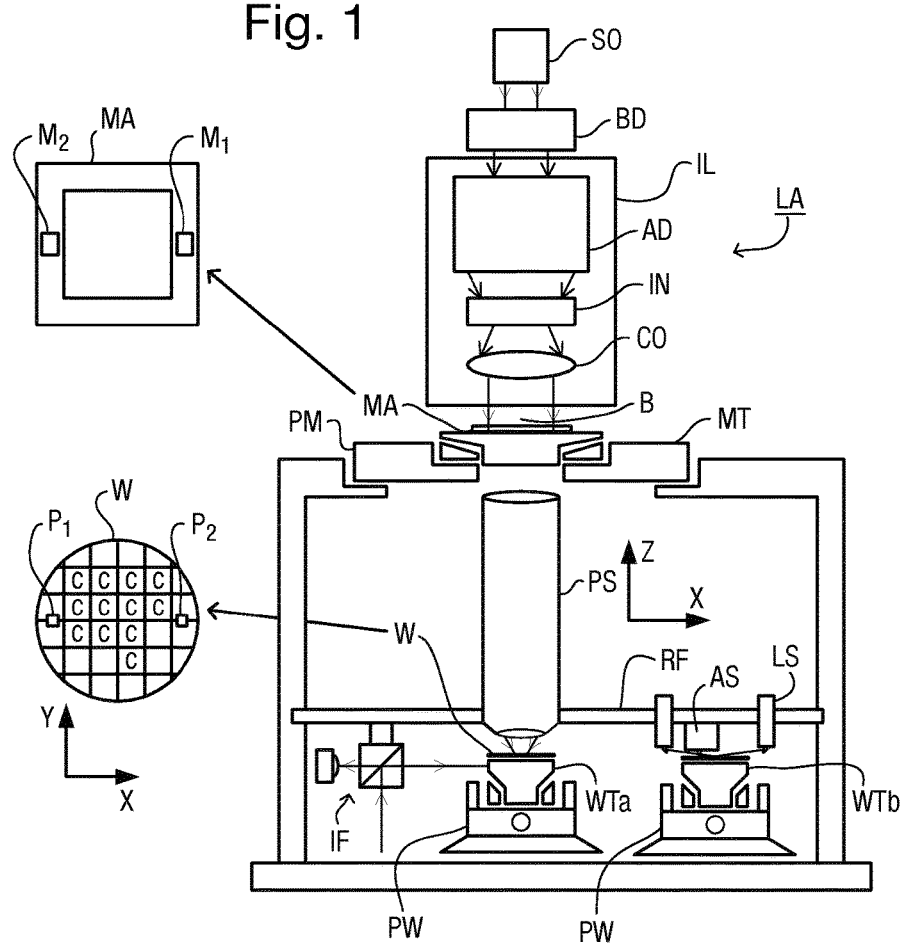
FIG. 1 depicts a lithographic apparatus according to an embodiment of the invention.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan. In general, movement of the patterning device support (e.g., mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g., mask table) MT may be connected to a short-stroke actuator only, or may be fixed.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. The alignment system, which detects the alignment markers, is described further below.

The depicted apparatus could be used in at least one of the following modes:

1. In step mode, the patterning device support (e.g., mask table) MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g., mask table) MT and the substrate table WT are scanned synchronously while a pattern imparted to the radiation beam is projected onto a target portion C (i.e., a single dynamic exposure). The velocity and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g., mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Lithographic apparatus LA is of a so-called dual stage type which has two substrate tables WTa, WTb and two stations—an exposure station and a measurement station—between which the substrate tables can be exchanged. While one substrate on one substrate table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS. This enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations.

Figure 2:
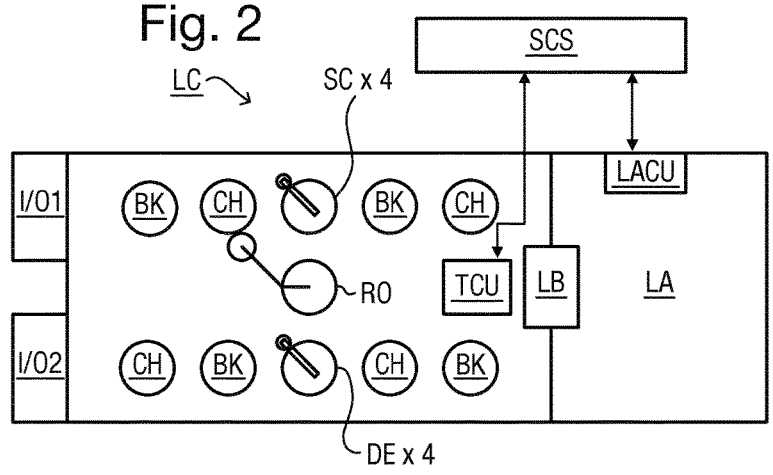
FIG. 2 depicts a lithographic cell or cluster according to an embodiment of the invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

Figure 3A:
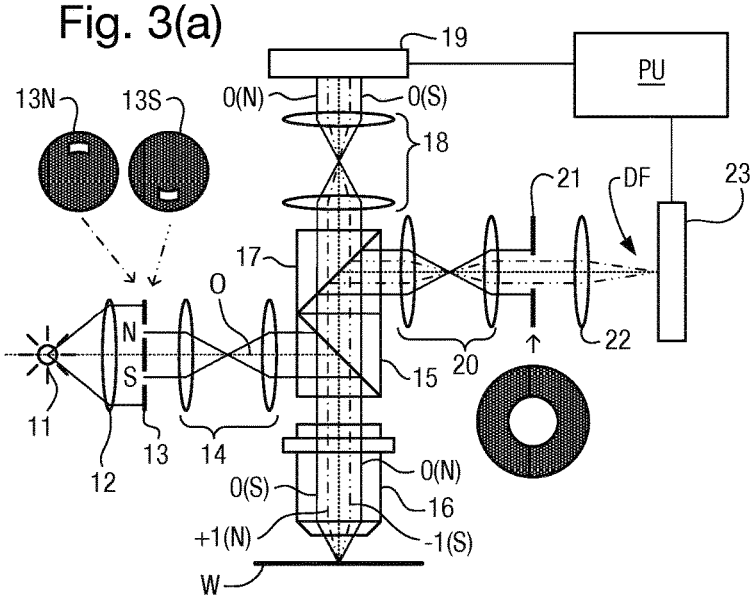
FIG. 3 comprises (a) a schematic diagram of a dark field scatterometer for use in measuring targets according to embodiments of the invention using a first pair of illumination apertures, (b) a detail of diffraction spectrum of a target grating for a given direction of illumination (c) a second pair of illumination apertures providing further illumination modes in using the scatterometer for diffraction based overlay measurements and (d) a third pair of illumination apertures combining the first and second pair of apertures.

A dark field metrology apparatus suitable for use in embodiments of the invention is shown in FIG. 3(a). A grating target T and diffracted rays are illustrated in more detail in FIG. 3(b). The dark field metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 (e.g., a xenon lamp) is directed onto substrate W via a beam splitter 15 by an optical system comprising lenses 12, 14 and objective lens 16. These lenses are arranged in a double sequence of a 4F arrangement. A different lens arrangement can be used, provided that it still provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

Figure 3B:
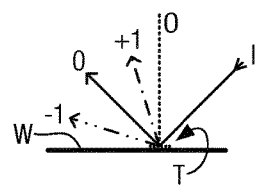

As shown in FIG. 3(b), grating target T is placed with substrate W normal to the optical axis O of objective lens 16. A ray of illumination I impinging on target T from an angle off the axis O gives rise to a zeroth order ray (solid line 0) and two first order rays (dot-chain line +1 and double dot-chain line −1). It should be remembered that with an overfilled small target grating, these rays are just one of many parallel rays covering the area of the substrate including metrology target T and other features. Where a composite grating target is provided, each individual grating within the target will give rise to its own diffraction spectrum. Since the aperture in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches and illumination angles can be designed or adjusted so that the first order rays entering the objective lens are closely aligned with the central optical axis. The rays illustrated in FIGS. 3(a) and 3(b) are shown somewhat off axis, purely to enable them to be more easily distinguished in the diagram.

At least the 0 and +1 orders diffracted by the target on substrate W are collected by objective lens 16 and directed back through beam splitter 15. Returning to FIG. 3(a), both the first and second illumination modes are illustrated, by designating diametrically opposite apertures labeled as north (N) and south (S). When the incident ray I is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A second beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for many measurement purposes such as reconstruction, which are not the subject of the present disclosure.

In the second measurement branch, optical system 20, 22 forms an image of the target on the substrate W on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to image processor and controller PU, the function of which will depend on the particular type of measurements being performed. Note that the term 'image' is used here in a broad sense. An image of the grating lines as such will not be formed, if only one of the −1 and +1 orders is present.

The particular forms of aperture plate 13 and field stop 21 shown in FIG. 3 are purely examples. In another embodiment of the invention, on-axis illumination of the targets is used, and an aperture stop with an off-axis aperture is used to pass substantially only one first order of diffracted light to the sensor. (The apertures shown at 13 and 21 are effectively swapped in that case.) In yet other embodiments, 2nd, 3rd and higher order beams (not shown in FIG. 3) can be used in measurements, instead of or in addition to the first order beams.

In order to make the illumination adaptable to these different types of measurement, the aperture plate 13 may comprise a number of aperture patterns formed around a disc, which rotates to bring a desired pattern into place. Alternatively or in addition, a set of plates 13 could be provided and swapped, to achieve the same effect. A programmable illumination device such as a deformable mirror array or transmissive spatial light modulator can be used also. Moving mirrors or prisms can be used as another way to adjust the illumination mode.

As just explained in relation to aperture plate 13, the selection of diffraction orders for imaging can alternatively be achieved by altering the pupil-stop 21, or by substituting a pupil-stop having a different pattern, or by replacing the fixed field stop with a programmable spatial light modulator. In that case the illumination side of the measurement optical system can remain constant, while it is the imaging side that has first and second modes. In the present disclosure, therefore, there are effectively three types of measurement method, each with its own advantages and disadvantages. In one method, the illumination mode is changed to measure the different orders. In another method, the imaging mode is changed. In a third method, the illumination and imaging modes remain unchanged, but the target is rotated through 180 degrees. In each case the desired effect is the same, namely to select first and second portions of the non-zero order diffracted radiation which are symmetrically opposite one another in the diffraction spectrum of the target. In principle, the desired selection of orders could be obtained by a combination of changing the illumination modes and the imaging modes simultaneously, but that is likely to bring disadvantages for no advantage, so it will not be discussed further.

Figure 3C:
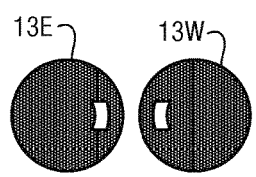

While the optical system used for imaging in the present examples has a wide entrance pupil which is restricted by the field stop 21, in other embodiments or applications the entrance pupil size of the imaging system itself may be small enough to restrict to the desired order, and thus serve also as the field stop. Different aperture plates are shown in FIGS. 3(c) and (d) which can be used as described further below.

Typically, a target grating will be aligned with its grating lines running either north-south or east-west. That is to say, a grating will be aligned in the X direction or the Y direction of the substrate W. Note that aperture plate 13N or 13S can only be used to measure gratings oriented in one direction (X or Y depending on the set-up). For measurement of an orthogonal grating, rotation of the target through 90° and 270° might be implemented. More conveniently, however, illumination from east or west is provided in the illumination optics, using the aperture plate 13E or 13W, shown in FIG. 3(c). The aperture plates 13N to 13W can be separately formed and interchanged, or they may be a single aperture plate which can be rotated by 90, 180 or 270 degrees. As mentioned already, the off-axis apertures illustrated in FIG. 3(c) could be provided in field stop 21 instead of in illumination aperture plate 13. In that case, the illumination would be on axis.

Figure 3D:
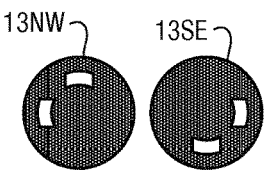

FIG. 3(d) shows a third pair of aperture plates that can be used to combine the illumination modes of the first and second pairs. Aperture plate 13NW has apertures at north and east, while aperture plate 13SE has apertures at south and west. Provided that cross-talk between these different diffraction signals is not too great, measurements of both X and Y gratings can be performed without changing the illumination mode.

Overlay Measurement Using Small Targets

Figure 4:
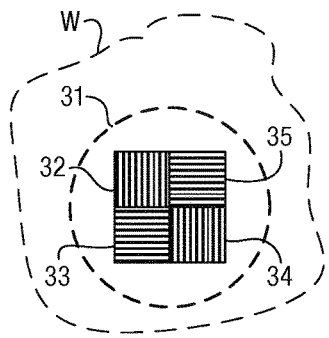
FIG. 4 depicts a multiple grating target and an outline of a measurement spot on a substrate.

FIG. 4 depicts a composite grating target formed on a substrate according to known practice. The composite target comprises four individual gratings 32 to 35 positioned closely together so that they will all be within a measurement spot 31 formed by the illumination beam of the metrology apparatus. The four targets thus are all simultaneously illuminated and simultaneously imaged on sensors 19 and 23. In an example dedicated to overlay measurement, gratings 32 to 35 are themselves composite gratings formed by overlying gratings that are patterned in different layers of the semi-conductor device formed on substrate W. Gratings 32 to 35 may have differently biased overlay offsets in order to facilitate measurement of overlay between the layers in which the different parts of the composite gratings are formed. Gratings 32 to 35 may also differ in their orientation, as shown, so as to diffract incoming radiation in X and Y directions. In one example, gratings 32 and 34 are X-direction gratings with biases of the +d, −d, respectively. This means that grating 32 has its overlying components arranged so that if they were both printed exactly at their nominal locations one of the components would be offset relative to the other by a distance d. Grating 34 has its components arranged so that if perfectly printed there would be an offset of d but in the opposite direction to the first grating and so on. Gratings 33 and 35 are Y-direction gratings with offsets +d and −d respectively. While four gratings are illustrated, another embodiment might require a larger matrix to obtain the desired accuracy. For example, a 3×3 array of nine composite gratings may have biases −4d, −3d, −2d, −d, 0, +d, +2d, +3d, +4d. Separate images of these gratings can be identified in the image captured by sensor 23.

Figure 5:
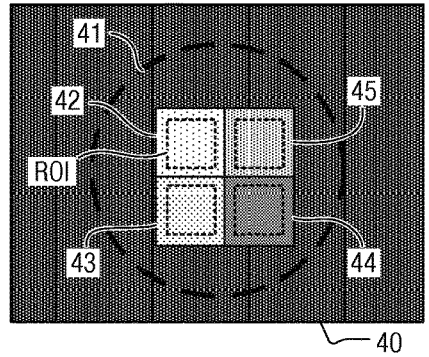
FIG. 5 depicts an image of the target of FIG. 4 obtained in the scatterometer of FIG. 3.

FIG. 5 shows an example of an image that may be formed on and detected by the sensor 23, using the target of FIG. 4 in the apparatus of FIG. 3, using the aperture plates 13NW or 13SE from FIG. 3(d). While the pupil plane image sensor 19 cannot resolve the different individual gratings 32 to 35, the image sensor 23 can do so. The cross-hatched rectangle 40 represents the field of the image on the sensor, within which the illuminated spot 31 on the substrate is imaged into a corresponding circular area 41. Ideally the field is dark. Within this dark field image, rectangular areas 42-45 represent the images of the individual gratings 32 to 35. If the gratings are located in product areas, product features may also be visible in the periphery of this image field. While only a single composite grating target is shown in the dark field image of FIG. 5, in practice a semiconductor device or other product made by lithography may have many layers, and overlay measurements are desired to be made between different pairs of layers. For each overlay measurement between pair of layers, one or more composite grating targets are required, and therefore other composite grating targets may be present, within the image field. Image processor and controller PU processes these images using pattern recognition to identify the separate images 42 to 45 of gratings 32 to 35. In this way, the images do not have to be aligned very precisely at a specific location within the sensor frame, which greatly improves throughput of the measuring apparatus as a whole. However the need for accurate alignment remains if the imaging process is subject to non-uniformities across the image field.

Once the separate images of the gratings have been identified, the intensities and/or other properties of those individual images can be measured, as discussed further below. Intensities and/or other properties of the images can be compared with one another. These results can be combined to measure different parameters of the lithographic process. Overlay performance is an important example of such a parameter. Application US 2011/027704 describes how overlay error between the two layers containing the component gratings 32 to 35 can be measured through asymmetry of the gratings, as revealed by comparing the intensities of regions of interest ROI 42-45 in the +1 order and −1 order dark field images.

Note that, by including only half of the first order diffracted radiation in each image, the 'images' referred to here are not conventional dark field microscopy images. Each grating will be represented simply by an area of a certain intensity level. The individual grating lines will not be resolved, because only one of the +1 and −1 order diffracted radiation is present. Particularly around the edges of the individual grating images, intensity values can be highly dependent on process variables such as resist thickness, composition, line shape, as well as edge effects generally.

In the prior applications, mentioned above, various techniques are disclosed for improving the quality of overlay measurements using the basic method mentioned above. For example, the intensity differences between images may be attributable to differences in the optical paths used for the different measurements, and not purely asymmetry in the target. The illumination source 11 may be such that the intensity and/or phase of illumination spot 31 are not uniform. Corrections can the determined and applied to minimize such errors, by reference for example to the position of the target image in the image field of sensor 23. The individual component gratings may be elongated in their direction of periodicity, so as to maximize the useful diffraction signals within a given target area. These techniques are explained in the prior applications, and will not be explained here in further detail. They may be used in combination with the techniques newly disclosed in the present application, which will be described below.

In US 2013/0771740, features in and around edge portions of the individual gratings are modified so as to reduce the intensity and extent of edge effects. These modifications may work in a similar way to optical proximity correction (OPC) features used to enhance the printing of fine features in a lithographic process. In US 2013/0258310, it is proposed to use three or more component gratings to measure overlay. By measuring asymmetries for gratings with at least three different biases, it is possible to correct for feature asymmetry in the target gratings, such as is caused by bottom grating asymmetry in a practical lithographic process. These techniques similarly are explained in the prior applications, and will not be explained here in further detail. They may be used in combination with the techniques newly disclosed in the present application, which will be described below.

While FIG. 5 shows an idealized image with four squares 42-45 of uniform intensity, in practice, however, the image of each grating on the camera is not perfect. Due to the nature of the dark-field imaging, the edges of the target light up more brightly than the center part. This makes it difficult to measure "the" intensity of the target. Furthermore, light contribution from the neighboring grating, or the surrounding, needs to be avoided. In order to address this problem, the region of interest (ROI) mentioned above has been defined to exclude the edges, and only select light from the central part of each of the four component gratings. In the prior proposal, an intensity value is obtained by averaging pixel values within the ROI. However, this means that effectively the signal is collected from a smaller area than the full size of the gratings. For example, where the individual gratings are 5×5 µm square, the ROI may correspond to only a 3×3 µm square area in the middle of the grating image. This decrease in signal either needs to be compensated with a longer acquisition time or results in a larger measurement uncertainty. Furthermore, correct placement of the ROI on the grating is extremely critical. A small shift will result in part of the edge light being included, which will lead to relatively large changes in the detected intensity and thus deteriorate measurement precision and accuracy further. Placement of the ROI may be predetermined or based on pattern recognition.

The target image is also subject to noise, which has been assumed to be random. The averaging across the ROI aims to suppress the effect of the noise. However, the present inventors have determined that the noise in the spatially filtered dark field image is not all random. Systematic oscillations are present in the image. As a result, simple averaging over a ROI, the dimensions of which do not match the period of the systematic oscillations in the image, gives a value that depends on the exact ROI position with respect to the position of the image of the small grating.

The exact grating position is controlled only with limited positioning accuracy, typically in the 200-nm-range, while gratings may have 5×5 µm$^2$ dimensions. The effective camera pixel size (at substrate level), which may be in the range of from 100 to 400 nm or less, may also influence the accuracy with which the rectangular ROI is able to match the exact period of the oscillation in the image.

Additionally, the edges of the small gratings often present heavy oscillations, which may be caused by a combination of one or more of: asymmetry in the grating, asymmetric illumination, asymmetric detection and optical vignetting, focus position, and possibly the exact position within the illumination spot.

Generally the ROI is chosen to have the largest size possible so as to optimize for signal-to-noise ratio. This means the ROI is located close to, but just excluding the edge regions. Therefore, any position inaccuracy of the ROI may include some of the pronounced edge oscillations, which significantly changes the estimated average 1st diffraction order intensity. The smaller the target and grating dimensions, the larger this effect will be, because the ratio of the 'flat' grating area to the edge area will reduce accordingly.

These effects have negative impact on the reproducibility and/or accuracy of the measurement.

Furthermore, the pattern-recognition of the target with standard pattern-recognition software often results in inaccurate positioning. This may be caused by the pronounced edge effects, as well as by the changing target image over the substrate related to the overlay, the focus and the stack dependence of the image of the gratings and the target. As a result, location of the correct ROI-position is error-prone. This holds especially for the extreme recipe settings, i.e. for wavelength-pitch ratios for which only a small part of the 1st diffraction order is transmitted to the camera, resulting in a limited spatial frequency content to 'build up' the sensor image, and consequently with clearer oscillations and edge effects as a result.

The oscillation effects also become more pronounced in the dark-field image, if grating- and target-dimensions are reduced. The oscillations are believed to be intrinsic in the metrology image, due to the fact that the targets are smaller than the field-of-view and the unavoidable Fourier-filtering that occurs in any realistic optical imaging system that filters out single orders. Smart target-design may reduce the oscillation amplitude in the image by reducing the edge-effects. However, the oscillations are believed to remain present due to the combination of small gratings and Fourier-filtering.

In this disclosure we propose a new approach to deriving a measurement of a property of interest from the measured image. This invention proposes to use physics-based few parameter fit-functions for improved signal estimation in dark-field metrology, such as overlay metrology, dose metrology, focus metrology or differential CD-metrology. The term "few parameter" is used herein to mean that the number of parameters (or coefficients) is very much less than the number of data points.

According to the invention, a combination fit function is proposed, optionally including a term representing imaging effects of the imaging system. The combination fit function can be applied to the whole of or a part of the measured image. The imaging effects can be effects of either or both of: the imaging branch of the metrology apparatus, and the sensor 23. In an embodiment of the invention, knowledge of the sensor and of the target design is used to select or construct a combination fit function and fix a number of the fit-parameters, such that the systematics (oscillations) in the measured image are well described. Then, only a small number of parameters need to be fitted to the measured data. The remaining component of the image consists only of random-noise, which can be dealt with using standard noise-filtering techniques. In an embodiment, a single fit-parameter then yields the desired diffraction order intensity for each grating. In an embodiment, the selection of ROI is dispensed with and the combination fit function is applied to the whole measured image. In an embodiment an ROI is used, but is selected to be larger than the grating image.

Advantages of an embodiment of the invention can include:
- The signal-estimation is independent of the exact ROI-position, because oscillations in the signal are fitted, not averaged.
- Noise-filtering techniques are applied only to the random noise component, and not applied to the systematic noise components, which are fitted by the combination fit function.
- The parameters that describe the edges yield information on the circumstances of the measurement, such as defocus, and can enable control of focus during the acquisition.
- Leakage of light to neighboring structures in the target-image due to Fourier filtering (optical cross-talk) may be taken into account by the tail of the combination fit-function into a neighboring ROI, therefore yielding a more accurate parameter estimate, e.g. for overlay.

The present invention is particularly useful with more extreme settings of the metrology apparatus (extreme λ/pitch-combinations), with 1$^{st}$ orders being cut-off by the pupil-stop, as they are expected to present the most pronounced oscillations and edge-effects.

Before describing details of specific embodiments and proposed combination fit-functions, some physical considerations are discussed.

In dark-field metrology, a single diffraction order image is projected on sensor 23 after spatial filtering (Fourier filtering) of its angle-resolved spectrum. The Fourier-filter can be implemented with a pupil-stop 21 with a numerical aperture NA≈0.41 (value projected to the back-focal plane of the objective).

This pupil-stop 21 limits the band of spatial frequencies that can build up the subsequently projected image. Consequently, the dark-field image could be (re-)constructed using a coherent and/or incoherent sum of sines and cosines corresponding to the spatial frequencies transmitted to the sensor 23, possibly with input from the pupil image sensor 19 as weighing coefficients. This leads to a significant number of fit-parameters, i.e. all coefficients for the sine- and cosine-series.

The properties of the optical imaging of the wafer onto the sensor 23 may also be expressed by a transfer function, such as the point-spread-function (PSF), which is basically the Fourier-transform of the limiting aperture: the pupil-stop 21 in the simplest case. The Fourier-transform of a circular pupil-stop is a jinc-function, which is a function of the pupil-stop diameter and the imaging wavelength. Alternatives to the point-spread-function include the modulation transfer function (MTF) and the optical transfer function (OTF). The dark-field image of a rectangular grating can also be thought of an incoherent sum of Airy-disks (squared jinc-functions) distributed over the field-of-view.

In the invention, it is proposed to use a few-parameter fit-function that captures correctly the frequency behavior over the grating image. The characteristic frequency is given by the optical properties of the sensor and the measurement settings.

The above described physical pictures have in common that they result in a typical (maximum) spatial frequency in the dark-field image. This spatial frequency will be used hereafter to construct artificial fit-functions with only a few fit-parameters that are suitable for fitting the dark-field image. The spatial frequency is characterized by the period p in the camera image plane:

$$p = \frac{a \cdot \lambda}{2 \cdot NA_{pupil\ stop}} \text{ with constant } a \text{ in the range of from } a = 1 \text{ to } 1.22 \quad (1)$$

where a=1.22 stems from the Rayleigh criterion for optical resolution (or the distance to the 1st node), and a=1 from the Fourier transform of the pupil-aperture. For example, the typical oscillation period yields p≈950 nm, for λ=650 nm and the pupil-stop NA≈0.41 and a=1.22. Note that the oscillation period in the dark-field image should not be confused with the grating pitch because the grating lines are not resolved.

First Embodiment

Figure 6:
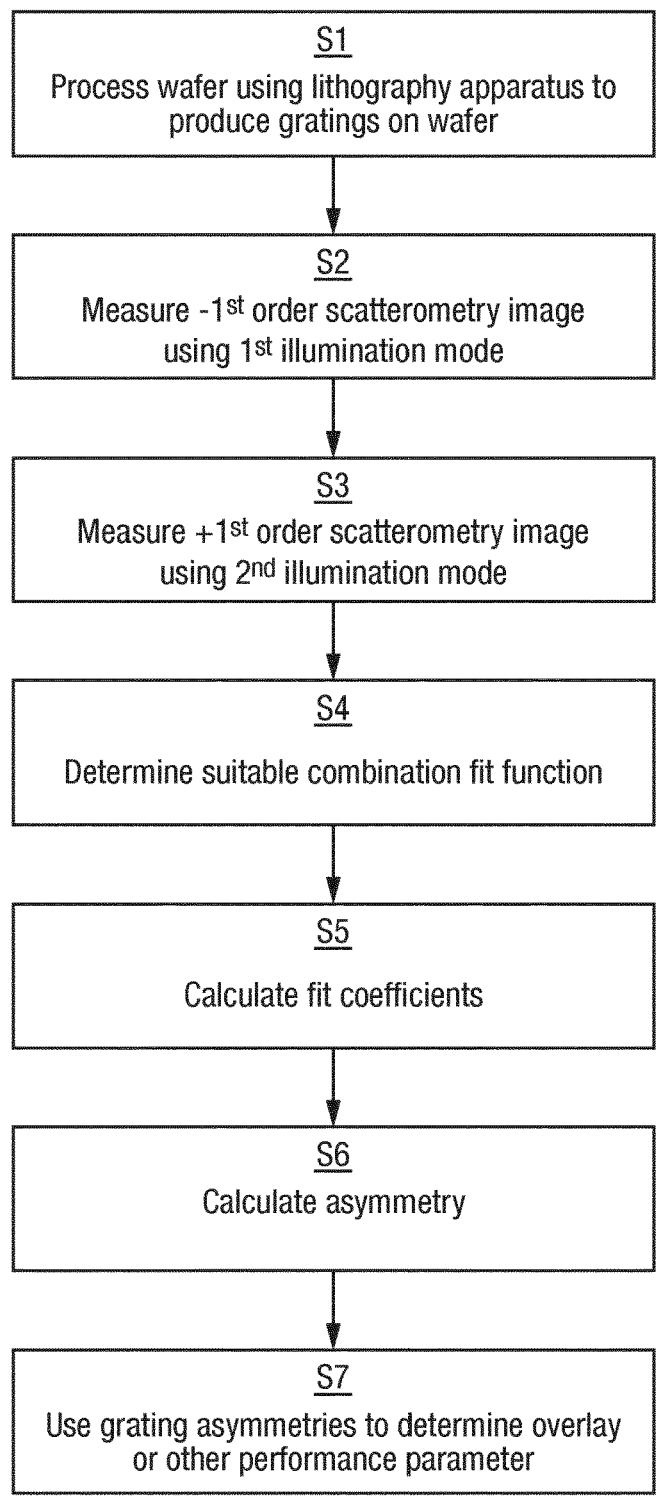
FIG. 6 is a flowchart showing the steps of an overlay measurement method using the scatterometer of FIG. 3 according to an embodiment of the present invention.

A method according to a first embodiment of the invention is described with reference to FIG. 6, which is a flow chart depicting selected steps of the method.

At step S1, the substrate, for example a semiconductor wafer, is processed through the lithographic cell of FIG. 2 one or more times, to create a structure including the overlay targets 32-35. At S2, using the metrology apparatus of FIG. 3, an image of the gratings 32 to 35 is obtained using only one of the first order diffracted beams (say −1). Then, whether by changing the illumination mode, or changing the imaging mode, or by rotating substrate W by 180° in the field of view of the metrology apparatus, a second image of the gratings using the other first order diffracted beam (+1) can be obtained (step S3). Consequently the +1 diffracted radiation is captured in the second image.

In step S4, a suitable combination fit function is selected or constructed. In an embodiment, the combination fit function depends on characteristics or parameters of the metrology apparatus, the layout of the target on the substrate, as well as the "recipes" for the metrology process and the lithographic process(es) used to form the target. The combination fit function comprises a plurality of terms, each term comprising one or more coefficients. Selection of a suitable combination fit function can be from a library of such functions. Construction of a combination fit function can be done by setting appropriate values to the coefficients. A term can be excluded (or de-selected) from the combination fit function by setting a relevant coefficient to zero. Values of some of the coefficients can be determinable based on the characteristics or parameters of the metrology apparatus and/or the metrology process recipe and/or the lithographic process recipe(s).

In an embodiment of the invention, terms of the combination fit function represent respective physical aspects of the measurement apparatus and process and/or the target being measured. Some coefficients for a term are determined from relevant characteristics or parameters of the respective physical parameters. Other coefficients are floating coefficients and will be found by the fitting step. For example, a combination fit function includes a term representing imaging effects. This term may include coefficients relating to the wavelength of the radiation used in imaging and/or the numeric aperture (NA) of the imaging system. A coefficient relating to the wavelength of the radiation may be a constant if the radiation source used is a monochrome source with a constant wavelength output. On the other hand, if the apparatus has an adjustable pupil, a coefficient relating to the numeric aperture may be a variable determined by the metrology process recipe. Other terms and/or coefficients may relate to the position and dimensions of the target and are selected or determined with reference to the lithographic process recipe. Further examples of terms and coefficients will be described further below. The determination of the fit function can, in an embodiment, be carried out in advance of steps S1 to S3. Where a plurality of similar or nominally identical targets on one or more substrates are to be measured, the selection or construction of a combination fit function can be carried out once, or once per batch of substrates processed.

In addition to the determinable coefficients, that is those which can be determined in advanced based on the characteristics or parameters of the metrology apparatus and/or the metrology process recipe and/or the lithographic process recipe(s), the combination fit function includes at least one floating coefficient. The floating coefficient, or at least one of the floating coefficients if there are a plurality of floating coefficients, relates to a characteristic of the target that is to be measured, e.g. asymmetry in the case of an overlay target. Other floating parameters may relate to noise and/or edge effects. The values for the floating parameter(s) is (are) determined in step S5 by a fitting process so that the combination fit function matches the measured image data. Conventional fitting processes, including iterative process, can be used. In an embodiment, a non-linear optimization algorithm is used. The desired accuracy by which the combination fit function is made to match the measured data can be determined for a specific application. In the event that a sufficiently accurate match cannot be achieved the grating may be re-measured or rejected as damaged.

Having found values for the floating coefficient(s) the property of interest for the target is determined. In the case of an overlay measurement, the target may include a plurality of gratings and the floating coefficients may include a floating coefficient related to the overall intensity of the radiation reflected from each grating into the respective order. By comparing the relevant fit coefficients obtained for the $-1^{st}$ first order scatterometry image and for the $+1^{st}$ first order scatterometry image, a measurement of asymmetry of the target grating is obtained in step S6. In step S7 the asymmetry measurement is used to calculate overlay. Overlay may be calculated in orthogonal directions using differently oriented gratings. Other parameters—such as focus, CD, dose or asymmetry—can be determined using the same process but with different targets designed to be sensitive to the relevant parameter.

In the first embodiment of the invention, the combination fit function for the dark-field image of a rectangular grating is given by:

$$I(x, y) = \left\{ c_0 + c_{x1} \, jinc\left(\frac{2\pi}{p}(x - x_1)\right) + c_{x2} \, jinc\left(\frac{2\pi}{p}(x - x_2)\right) + \right.$$
$$c_x \sin\left(\frac{2\pi}{p}(x - x_0)\right) + c_{y1} \, jinc\left(\frac{2\pi}{p}(y - y_1)\right) +$$
$$\left. c_{y2} \, jinc\left(\frac{2\pi}{p}(y - y_2)\right) + c_y \sin\left(\frac{2\pi}{p}(y - y_0)\right) \right\} \times w(x, y) \quad (2)$$

This combination fit function is built-up from a constant term $c_0$, which is a measure for the average intensity of the diffraction order of that grating, jinc-functions at the four edges of the grating, a sine-function that can have a different phase $x_0$ compared to the jinc-functions, and a window function $w(x,y)$ over the whole grating.

Figure 7:
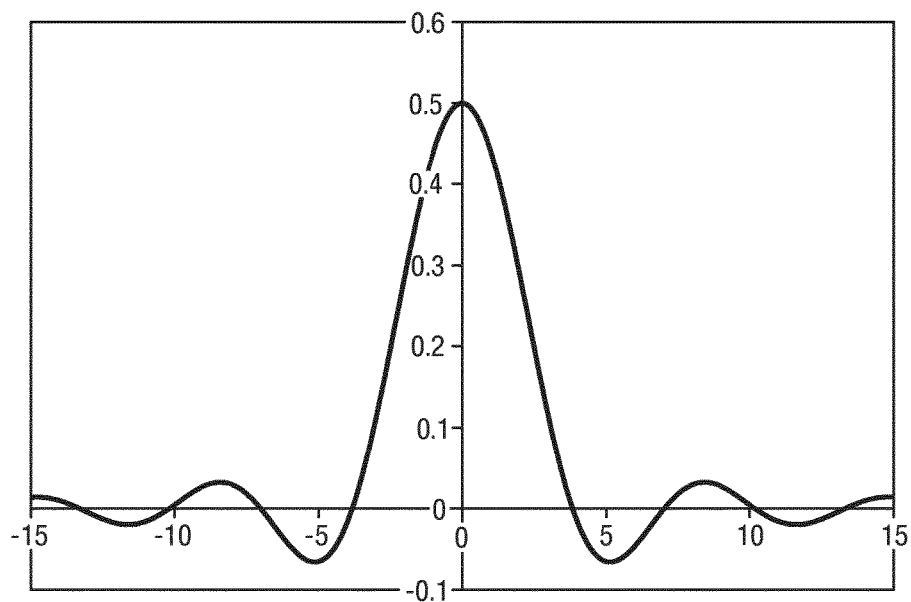
FIG. 7 is a graph of a jinc function that can be used in embodiments of the present invention.

The jinc function can be defined as $$jinc(x) = \frac{J_1(x)}{x}$$

where $J_1(x)$ is a Bessel function of the first kind and satisfies $\lim_{x \to 0} jinc(x) = 1/2$. Alternatively a factor of 2 can be included so the limit of the function at 0 is 1. The form of jinc (x) for x=−15 to +15 is shown in FIG. 7. The jinc functions are examples of terms representing the imaging effects of the measurement branch since the jinc function is the Fourier transform of the circular pupil stop 21. The determinable coefficients $x_1$, $x_2$, $y_1$ and $y_2$ relate to the positions of the edges of the grating. For alternative shapes of the aperture, e.g. ¼ of a circularly shaped aperture, different edge-functions may be desirable. For example, if a 4-quadrant wedge is used as the pupil filter, the jinc function could be replaced by the Fourier transform of a quarter circle. Also approximate edge-functions, such as the sinc-function (sin x/x) or Fraunhofer function (Fourier transform of a rectangular shape), can be used in embodiments of the invention.

The window function may be taken for example to be Gaussian function, falling off outside the grating area:

$$w(x, y) = w(x)w(y) \quad (3)$$

-continued $$w(x) = \begin{cases} \exp\left(-\frac{1}{2}\left(\frac{x-x_1+b\lambda}{\sigma}\right)^2\right), & x < x_1 - b\lambda \\ \exp\left(-\frac{1}{2}\left(\frac{x-x_2-b\lambda}{\sigma}\right)^2\right), & x > x_2 + b\lambda \\ 1 & \text{elsewhere} \end{cases}$$

and $$w(y) = \begin{cases} \exp\left(-\frac{1}{2}\left(\frac{y-y_1+b\lambda}{\sigma}\right)^2\right), & y < y_1 - b\lambda \\ \exp\left(-\frac{1}{2}\left(\frac{y-y_2-b\lambda}{\sigma}\right)^2\right), & y > y_2 + b\lambda \\ 1 & \text{elsewhere} \end{cases}$$

where $\sigma$ defines the strength of the fall-off of the window function and can be determined experimentally, and b defines the exact position of the window-functions with respect to the grating edge-positions and the jinc-function positions.

In an embodiment x and y shift parameters can be added to the combination fit-function, to compensate for misalignment, for example caused by inaccurate pattern recognition. As a result of a defocussed wafer, the position of the grating dark-field images may shift for x- and y-gratings differently. This grating-direction dependent shift may easily be included in the combination fit function with two additional parameters for the x- and y-directions respectively.

Figure 8:
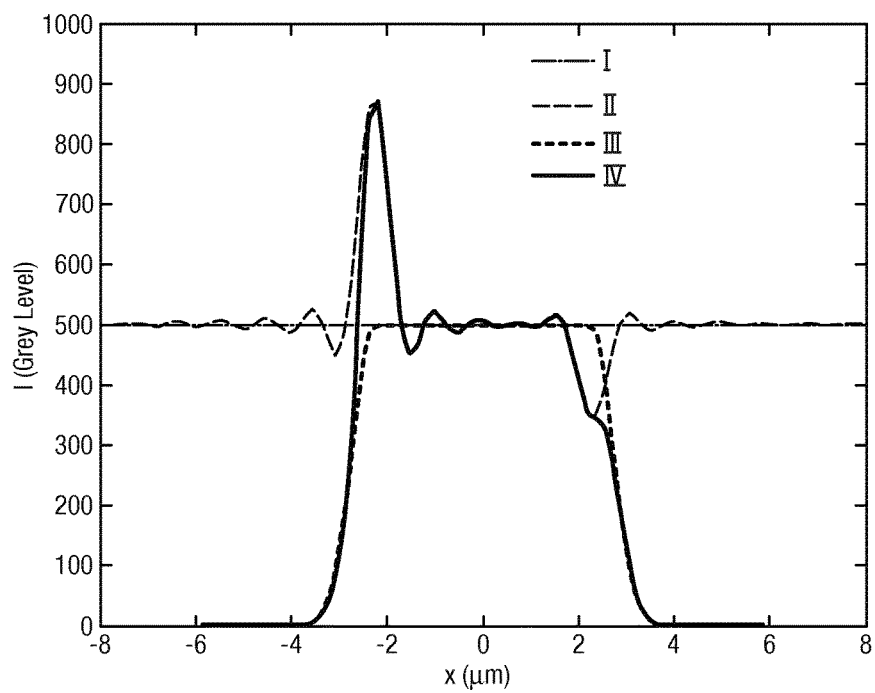
FIG. 8 is a graph illustrating a combination fit function according to an embodiment of the present invention

FIG. 8 presents an example single-line fit-function for arbitrarily chosen parameter values using equations (2) and (3). In FIG. 8, the dot-chain line I represent the constant value $c_0$, long dashed line II represents the sum of 2 jinc functions and $c_0$, short dashed line III represents the scaled window function w and solid line IV represents the combination fit function. For a hypothetical 5 μm wide grating, the fit-parameters are: $c_0=500$, $c_{x1}=380$, and $c_{x2}=-150$, with $b\lambda=120$ nm and $\sigma=0.45$ times the oscillation pitch.

In the case where multiple gratings are simultaneously imaged (e.g. two x-gratings and two y-gratings), a whole-image fit function can be constructed using a combination fit function such as that of equation (2) for each grating. Parameters $x_1$, $x_2$, $y_1$ and $y_2$ are then given by the position of each grating, e.g. from the GDS-design of the target, and the oscillation pitch p and wavelength $\lambda$ are given from the optics from the sensor and the measurement wavelength. Parameters b and $\sigma$ are assigned fixed values per measurement, or series of measurements, in equation (3).

The remaining fit-parameters (floating coefficients) are then in this case:
1. $c_0$: a measure for the diffraction efficiency from the grating (parameter of interest)
2. $c_{x1}$, $c_{x2}$, $c_{y1}$, $c_{y2}$: the describing the edge effects, and oscillations in the center of the grating
3. $c_x$, $c_y$, $x_0$, $y_0$: tuning parameters for small deviations from the resulting curves from the above-mentioned parameters.

For a complete target in an example, this will yield 4×5=20 fit-parameters for each target measurement, assuming the grating positions are determined.

An example comparing a measurement of a target is given below in FIGS. 9 and 10, where the grating pitch was 600 nm and the measurement wavelength $\lambda=650$ nm. Note that only a quick manual tuning of the parameters has been performed but is sufficient to reproduce all features and oscillations.

Figure 9:
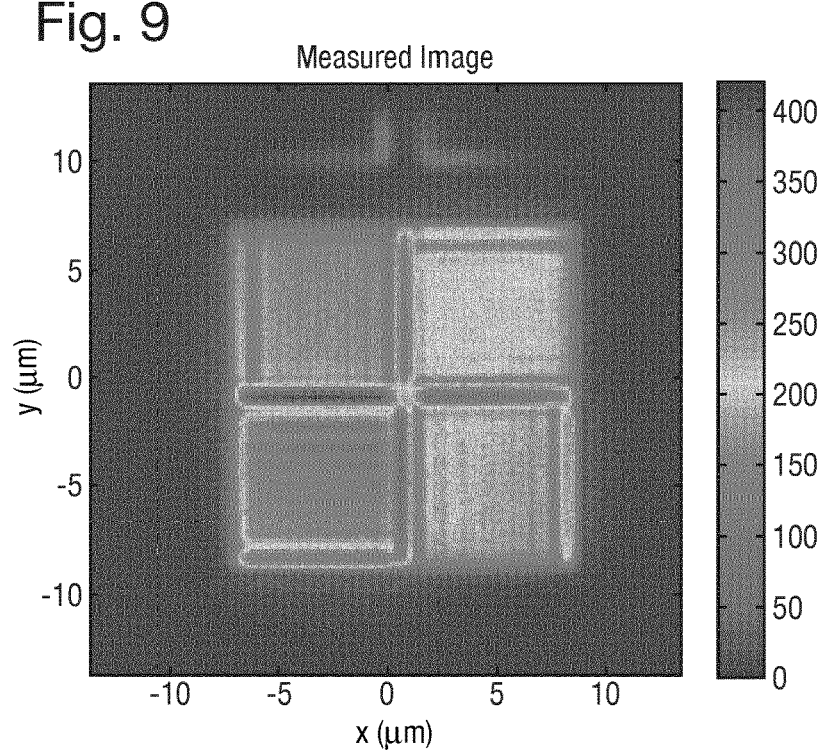
FIG. 9 depicts a measured dark field scatterometry image.
Figure 10:
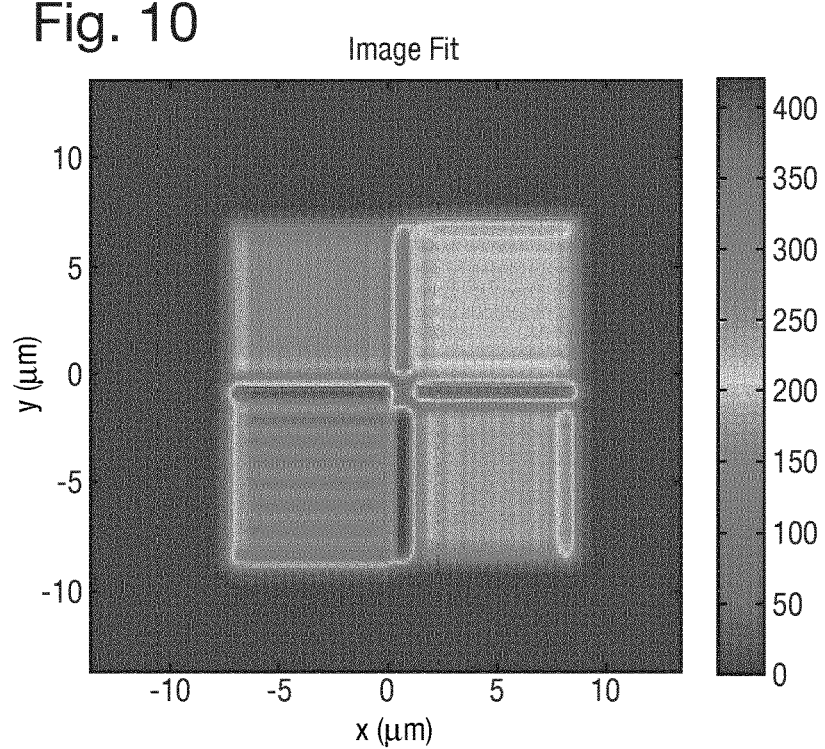
FIG. 10 depicts a dark field image simulated using combination fit functions according to an embodiment of the present invention.

FIG. 9 shows an image of a square target of the type shown in FIG. 4 and having dimensions 16 μm×16 μm and pitch=600 nm, measured at $\lambda=650$ nm for both polarizations, and FIG. 10 shows a corresponding synthetic image using equation (2) with a=1.22 in equation (1) and $c_x=c_y=0$. So, the image is built-up only of a constant per grating and 1D jinc-functions at the edges of each grating.

Figure 11:
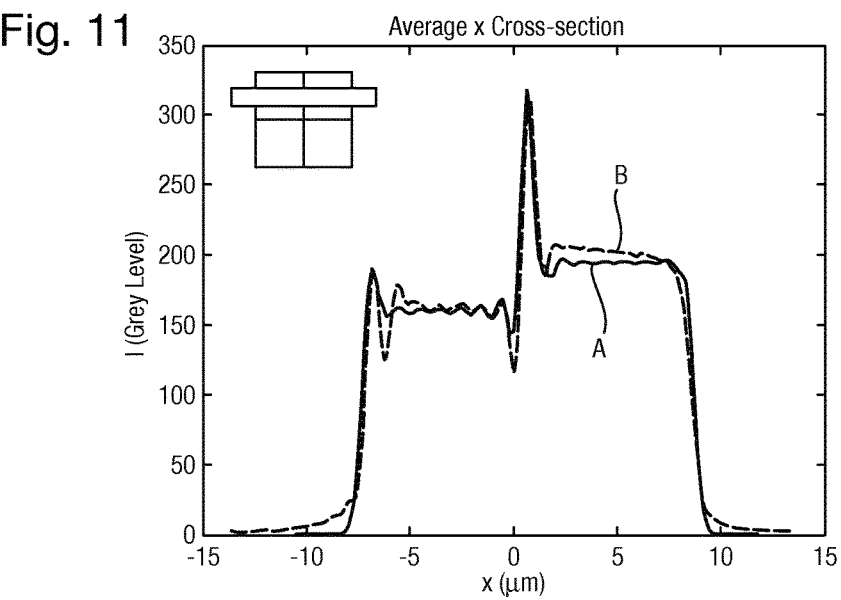
FIGS. 11 to 14 are graphs comparing measured and simulated intensities in particular regions of the images of FIGS. 9 and 10.
Figure 12:
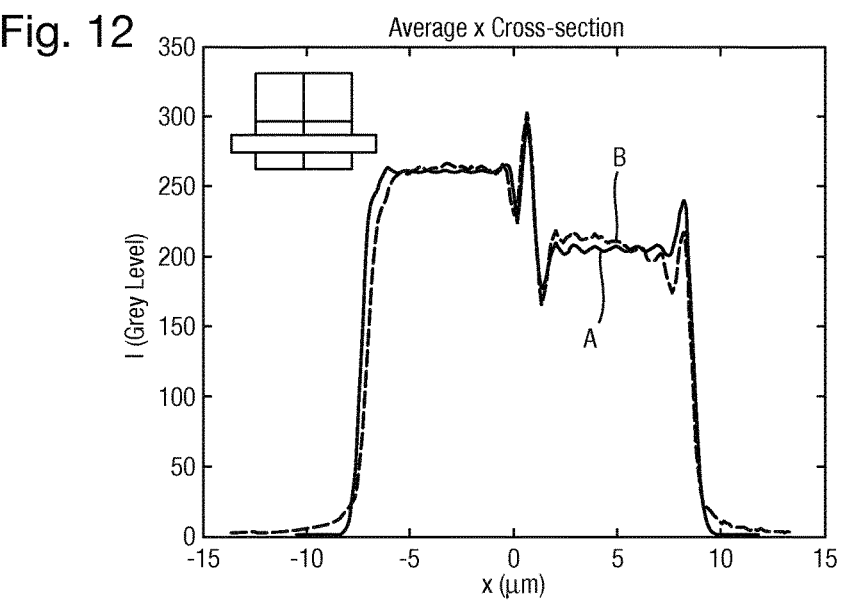
Figure 13:
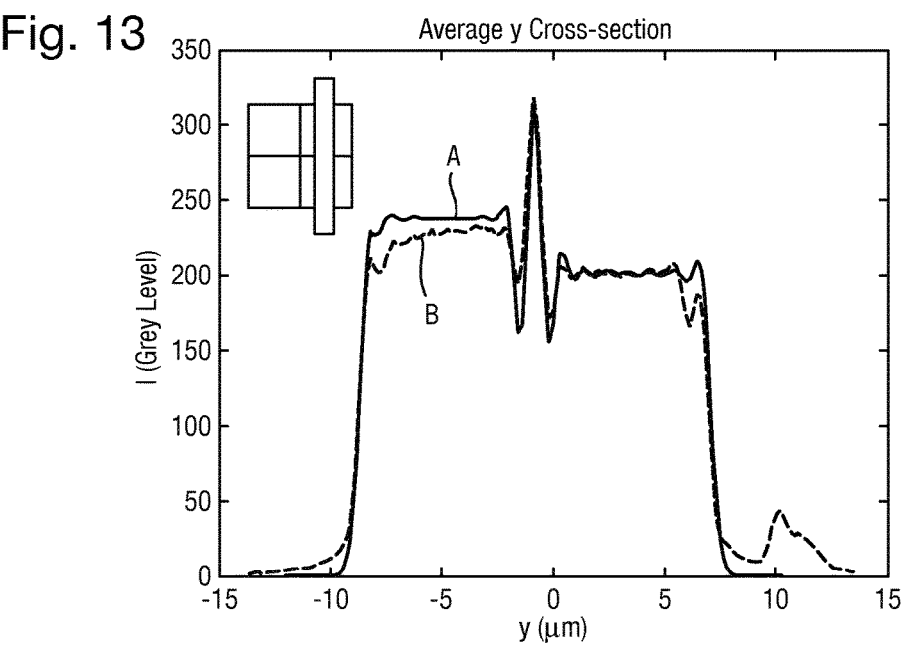
Figure 14:
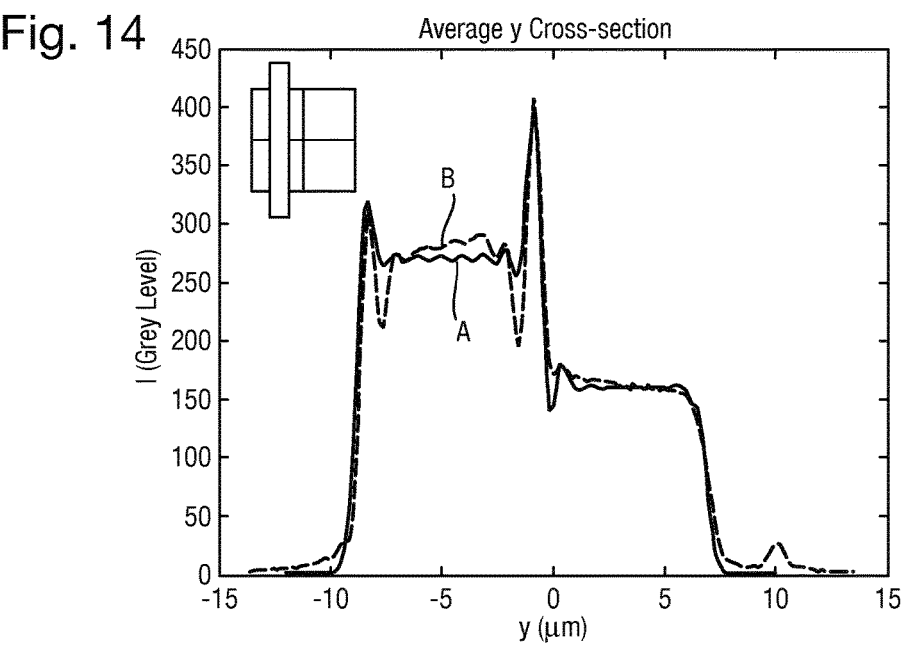

FIGS. 11 to 14 compare the synthetic fit-function image with the measured image from FIG. 9. FIGS. 11 and 12 are cross-sections in the x-direction averaged over the y-direction, and FIGS. 13 and 14 are cross-sections in the y-direction averaged over the x-direction. In FIGS. 11 to 14 the solid line labeled "A" represents the fit function and the dashed line labeled "B" represents the measured image data. Although a manual determination of the few parameters has been performed, the main characteristic oscillations are clearly reproduced. In an embodiment, further optimization of the fit, e.g. performed automatically, and use of the other floating parameters can provide a much closer fit to the measured image.

TABLE 1

| | Fit-parameters of equation (2), as used in FIGS. 10 and 11. | | | | | | | | | |
|---|---|---|---|---|---|---|---|---|---|---|
| grating | position | bias | $c_0$ | $c_{x1}$ | $c_{x2}$ | $c_{y1}$ | $c_{y2}$ | $x_0$ | $c_x$ | $y_0$ | $c_y$ |
| y | top-right | −d | 195 | −20 | −10 | 180 | 40 | 0 | 0 | 0 | 0 |
| x | top-left | +d | 160 | 30 | 140 | 15 | −15 | 0 | 0 | 0 | 0 |
| y | bottom-left | +d | 270 | −30 | 0 | 50 | 130 | 0 | 0 | 0 | 0 |
| x | bottom-right | −d | 180 | 240 | 80 | −20 | 5 | 0 | 0 | 0 | 0 |

In an embodiment of the invention, source illumination asymmetries (spot profiles) may be taken into account, as image corrections before the fitting, or taken into the fit-procedure as predetermined calibrated, constant profiles. This has not been taken into account here, and some small slopes over the gratings are observed in the measurement. If there are sensor imperfections, additional terms can be added to improve accuracy of the combination fit function.

The combination fit function of the 1st embodiment is an example. Other functions, such as a windowed sine-function restricted to the center-part of the gratings, may also be used. Such a windowed sine-function is described by setting the constant before the jincs to 0 in equation (2) and fitting the other parameters.

Also, more complex combination fit functions fall in the scope of this invention. For example, it is possible to include a second, slightly shifted jinc-function near one or more edges, to include effects of a double-step at the edges due to a shift between bottom and top-grating by design, or induced by a large overlay.

Second Embodiment

A second embodiment of the invention will now be described. The second embodiment is the same as the first embodiment except in relation to the combination fit function. For the sake of conciseness a description of common features is omitted below.

The second embodiment allows additional fit-parameters (floating coefficients) by use of a combination fit function in the form of a grid of squared jincs at the grating area:

$$I(x, y) = \sum_{ij} c_{ij} \left| jinc\left(\frac{2\pi}{p}\sqrt{(x-x_i)^2 + (y-y_j)^2}\right)\right|^2 \quad (4)$$

with grid spacing: $x_{i+1}-x_i=\Delta x$ and $y_{j+1}-y_j=\Delta y$

The grid spacing can, for example, be chosen consistent with the Nyquist sampling criterion (optical resolution). Alternatively, it can be more sparsely sampled to cover still the details of the measured image, using, for example, the oscillation frequency in the image from equation (1).

The combination fit function of the second embodiment can provide a synthetic image that is closer to the real measurement because of the use of the squared jincs, but contains more fit-parameters. The synthetic image naturally falls off next to the edges outside the grating area, as no squared jinc-function is located at such positions. Therefore, a window-function is not required in this approach. The extraction of the diffraction efficiency of the grating is given by the average of the squared- and displaced jincs, as there is no constant fit-parameter $c_0$.

Note that the jinc-function is given as example, resulting from the Fourier-transform of the circularly shaped pupil-filter. For other pupil-filter shapes, the jinc-function can be replaced by its appropriate Fourier-transform function.

Third Embodiment

A third embodiment of the invention will now be described. The third embodiment is the same as the first embodiment except in relation to the combination fit function. For the sake of conciseness a description of common features is omitted below.

In the third embodiment, the target image is reconstructed using a Fourier series, of which the weights of the spatial frequency component can be determined in agreement with simultaneously measured pupil-plane information. This can be implemented for each grating:

$$I(x, y) = \left(c_0 + \sum_{m,n} c_{m,n} \cdot e^{2\pi i \frac{m}{s} x} \cdot e^{2\pi i \frac{n}{t} y}\right) \times w(x, y) \quad (5a)$$

in which $c_0$ is again the diffraction efficiency, m and n are integers (positive and negative) with s and t the period in x and y directions respectively. The values m/s and n/t correspond to the frequencies transmitted by the pupil-filter. The period s and t can be chosen to correspond to the grating dimensions. In that case, the number of m and n values is limited between ±1 and the maximum frequency transmitted by the pupil-stop, which results in a larger number of fit-parameters $c_{mn}$ than for the $1^{st}$ embodiment. Equation (5a) solves separately for each grating in the field of view, of which the total of contributions should be in correspondence with the measured image. Alternatively, the whole image is constructed at once for all structures in the field of view:

$$I(x, y) = \sum_{m,n} c_{m,n} \cdot e^{2\pi i \frac{m}{s} x} \cdot e^{2\pi i \frac{n}{t} y} \quad (5b)$$

In the third embodiment, the noise that results in higher spatial frequencies than constrained by the pupil-filter, will be filtered out correctly.

In both equations (5a) and (5b), the frequency content m/s and n/t is again limited to the frequencies that are transmitted by the pupil-filter for a certain wavelength. This is sensor information that is known and fixed in advance. The periods s and t are in this case e.g. the total illumination spot size, or the total field of view. Then, the coefficients $c_{mn}$ are the fit-parameters.

Fourth Embodiment

In a fourth embodiment, the fit function is used to correct the image by subtracting the disturbances to leave a clean intensity signal. An intensity value is then derived from the clean intensity signal by any suitable method, e.g. averaging. The fourth embodiment can use any of the above combination fit function but is described with reference to the first combination fit function, equation (2). Having found values of the floating coefficients $c_o$, $c_{x1}$, $c_{x2}$, etc. a synthetic disturbance function is constructed from the disturbance terms, that is the edge effect terms (jincs) and the systematic noise terms (sines) and optionally the window function. This synthetic disturbance function is then subtracted from the measured pixel image data to generate the clean intensity signal.

CONCLUSION

The techniques disclosed herein enable the use of small metrology targets to achieve great accuracy and repeatability of overlay and other measurements. Particular benefits that may be realized in a particular implementation include:

Improved reproducibility, e.g. of overlay, by eliminating the systematics in the signal, leaving mainly random-noise signal components that can correctly be dealt with using algorithms developed for noise-filtering.

Improved reproducibility, e.g. of overlay, by reducing the impact of the positioning inaccuracy.

Improved reproducibility, e.g. of overlay, by inclusion of more pixels over the full grating for the determination of the 'average' intensity, compared to the small number of pixels within ROI-based signal estimation.

Improved pattern-recognition of the dark-field grating image, by using physics-based fit-functionality with a limited number of fit-parameters, which allows for a more stable recognition of a varying dark-field image over the measured semiconductor wafers.

Sensor-related illumination or detection light-variations over the field-of-view can be included as an additional parameter (e.g. an additional slope in the image) if desired, for correction for these effects. (e.g. chromatic vignetting effects).

Additional parameters indicating the circumstances of the measurement, for example, via the magnitude and sign of the jincs describing the edge effects, such as defocus during target acquisition. This may also be used for the correct focus level for the acquisition leading to improved accuracy and reproducibility.

The present invention is applicable to many different dark-field metrology techniques, in which a small grating is measured, such as overlay, focus, CD, dose, asymmetry.

It opens possibilities for more accurate parameter estimation, by cross-talk reduction of the light leakage between neighboring gratings, particularly for the first and second embodiments where e.g. the tail of the window-function combined with the jinc-function takes the cross-talk to the neighboring structure into account.

Less dummy pattern area around the target is needed, if ROI or pattern recognition is improved using the fit-functions, saving real-estate for metrology or improving reproducibility by elongating the grating area at the expense of the dummy area. The fit-function approach could similarly also be of use for target designs optimized to have very recognizable edge-effects on which the pattern-recognition is performed.

The technique is compatible with other techniques in small—target diffraction—based overlay measurement, that have been described in the recent patent applications mentioned above. For example, the techniques disclosed herein can be used with a wide variety of target types and properties, e.g. dimensions. The present invention is applicable to all camera image-based metrology techniques that contain parameter extraction from non-Gaussian or white-noise signals.

While the target structures described above are metrology targets specifically designed and formed for the purposes of measurement, in other embodiments, properties may be measured on targets which are functional parts of devices formed on the substrate. Many devices have regular, grating-like structures. The terms 'target grating' and 'target structure' as used herein do not require that the structure has been provided specifically for the measurement being performed.

In an embodiment, there is provided a method of measuring a property of a lithographic process, using a target structure that has been formed by the lithographic process on a substrate, the method comprising: forming an image of the target structure using an imaging system that selects a predetermined portion of radiation diffracted by the target structure under predetermined illumination conditions; measuring the image of the target structure; identifying one or more regions of interest in the measured image; and determining a value of at least one coefficient of a combination fit function using pixel values of the one or more regions of interest, wherein the value of the coefficient is indicative of the property of the lithographic process.

In an embodiment, the combination fit function includes an imaging term representing imaging effects of the imaging system. In an embodiment, the imaging term is based on a transfer function of the imaging system. In an embodiment, the imaging system includes an aperture and the imaging term is based on a transform of the aperture. In an embodiment, the imaging term includes a jinc function. In an embodiment, the target structure has an outline that has a plurality of edges and the combination fit function includes a respective imaging term for each of the edges. In an embodiment, the combination fit function includes a periodic function representing a disturbance. In an embodiment, the combination fit function includes a target term representing an ideal image of the target structure; and the coefficient is a coefficient of the target term. In an embodiment, the target term is a constant function and the coefficient is the value of the constant function. In an embodiment, the combination fit function includes a window function. In an embodiment, the combination fit function is of the form:

$$J(x, y) = \left\{ c_0 + c_{x1} jinc\left(\frac{2\pi}{p}(x-x_1)\right) + c_{x2} jinc\left(\frac{2\pi}{p}(x-x_2)\right) + c_x \sin\left(\frac{2\pi}{p}(x-x_0)\right) + c_{y1} jinc\left(\frac{2\pi}{p}(y-y_1)\right) + c_{y2} jinc\left(\frac{2\pi}{p}(y-y_2)\right) + \right.$$

-continued $$\left. c_y \sin\left(\frac{2\pi}{p}(y-y_0)\right) \right\} \times w(x, y)$$

where: x and y are Cartesian coordinates in the measured image; $c_i$, $x_0$ and $y_0$ are fit-coefficients; p is a typical spatial period in the image, $x_1$, $x_2$, $y_1$ and $y_2$ represent the positions of the edges of the target structure, and w is a window function. In an embodiment, the coefficient c0 represents the diffraction efficiency of a specific diffraction order of the target. In an embodiment, the window function w(x,y) is defined by:

$$w(x, y) = w(x)w(y)$$

$$\text{with } w(x) = \begin{cases} \exp\left(-\frac{1}{2}\left(\frac{x-x_1+b\lambda}{\sigma}\right)^2\right), & x < x_1 - b\lambda \\ \exp\left(-\frac{1}{2}\left(\frac{x-x_2-b\lambda}{\sigma}\right)^2\right), & x > x_2 + b\lambda \\ 1 & \text{elsewhere} \end{cases}$$

$$\text{and } w(y) = \begin{cases} \exp\left(-\frac{1}{2}\left(\frac{y-y_1+b\lambda}{\sigma}\right)^2\right), & y < y_1 - b\lambda \\ \exp\left(-\frac{1}{2}\left(\frac{y-y_2-b\lambda}{\sigma}\right)^2\right), & y > y_2 + b\lambda \\ 1 & \text{elsewhere} \end{cases}$$

In an embodiment, the combination fit function is of the form:

$$I(x, y) = \left| \sum_{ij} c_{ij} \right| jinc\left(\frac{2\pi}{p}\sqrt{(x-x_i)^2 + (y-y_j)^2}\right) \right|^2$$

where: x and y are Cartesian coordinates in the measured image; $c_{ij}$, $x_i$ and $y_j$ are fit-coefficients; and p is a typical spatial period in the image. In an embodiment, the combination fit function is of the form:

$$I(x, y) = \left( c_0 + \sum_{m,n} c_{mn} \cdot e^{2\pi i \frac{m}{s} x} \cdot e^{2\pi i \frac{n}{t} y} \right) \times w(x, y)$$

where: x and y are Cartesian coordinates in the measured image; $c_0, c_{mn}$, s and t are fit-coefficients; and w is a window function. In an embodiment, the target structure is a composite target structure including a plurality of component structures and the combination fit function includes a respective fit function for each of the component structures. In an embodiment, the target structure is a part of a structure of a device formed on the substrate. In an embodiment, the property is selected from the group consisting of: overlay, focus, dose, CD and asymmetry. In an embodiment, determining a value of at least one coefficient is performed using a non-linear optimization algorithm.

In an embodiment, there is provided an inspection apparatus for measuring a property of a lithographic process using a target structure that has been formed by the lithographic process on a substrate, the apparatus comprising: a support for the substrate having the target structure formed thereon; an illumination system for illuminating the composite target structure under predetermined illumination conditions; an imaging system for forming an image of the composite target structure using a predetermined portion of radiation diffracted by the component target structures under the illumination conditions; a measuring system for measuring the image; a processor arranged to identify one or more regions of interest in the detected image and to determine a value of at least one coefficient of a combination fit function using pixel values of the one or more regions of interest, wherein the value of the coefficient is indicative of the property.

In an embodiment, the combination fit function includes an imaging term representing imaging effects of the imaging system. In an embodiment, the imaging term is based on a transfer function of the imaging system. In an embodiment, the imaging system includes an aperture and the imaging term is based on a transform of the aperture. In an embodiment, the imaging term includes a jinc function. In an embodiment, the target structure has an outline that has a plurality of edges and the combination fit function includes a respective imaging term for each of the edges. In an embodiment, the combination fit function includes a periodic function representing a disturbance. In an embodiment, the combination fit function includes a target term representing an ideal image of the target structure; and the coefficient is a coefficient of the target term. In an embodiment, the target term is a constant function and the coefficient is the value of the constant function. In an embodiment, the combination fit function further includes a window function. In an embodiment, the combination fit function is of the form:

$$J(x, y) = \left\{ c_0 + c_{x1} jinc\left(\frac{2\pi}{p}(x - x_1)\right) + c_{x2} jinc\left(\frac{2\pi}{p}(x - x_2)\right) + c_x \sin\left(\frac{2\pi}{p}(x - x_0)\right) + \right.$$
$$c_{y1} jinc\left(\frac{2\pi}{p}(y - y_1)\right) + c_{y2} jinc\left(\frac{2\pi}{p}(y - y_2)\right) +$$
$$\left. c_y \sin\left(\frac{2\pi}{p}(y - y_0)\right) \right\} \times w(x, y)$$

where: x and y are Cartesian coordinates in the measured image; $c_i$, $x_0$ and $y_0$ are fit-coefficients; p is a typical spatial period in the image, $x_1$, $x_2$, $y_1$ and $y_2$ represent the positions of the edges of the target structure, and w is a window function. In an embodiment, the coefficient co represents the diffraction efficiency of a specific diffraction order of the target. In an embodiment, the window function w(x,y) is defined by:

$$w(x,y) = w(x) \, w(y)$$

with $w(x) = \begin{cases} \exp\left(-\frac{1}{2}\left(\frac{x - x_1 + b\lambda}{\sigma}\right)^2\right), & x < x_1 - b\lambda \\ \exp\left(-\frac{1}{2}\left(\frac{x - x_2 - b\lambda}{\sigma}\right)^2\right), & x > x_2 + b\lambda \\ 1 & \text{elsewhere} \end{cases}$ and $w(y) = \begin{cases} \exp\left(-\frac{1}{2}\left(\frac{y - y_1 + b\lambda}{\sigma}\right)^2\right), & y < y_1 - b\lambda \\ \exp\left(-\frac{1}{2}\left(\frac{y - y_2 - b\lambda}{\sigma}\right)^2\right), & y > y_2 + b\lambda \\ 1 & \text{elsewhere} \end{cases}$ In an embodiment, the combination fit function is of the form:

$$I(x, y) = \sum_{ij} c_{ij} \left| jinc\left(\frac{2\pi}{p}\sqrt{(x - x_i)^2 + (y - y_j)^2}\right) \right|^2$$

where: x and y are Cartesian coordinates in the measured image; $c_{ij}$, $x_i$ and $y_j$ are fit-coefficients; and p is a typical spatial period in the image. In an embodiment, the combination fit function is of the form:

$$I(x, y) = \left( c_0 + \sum_{m,n} c_{mn} \cdot e^{2\pi i \frac{m}{s} x} \cdot e^{2\pi i \frac{n}{t} y} \right) \times w(x, y)$$

where: x and y are Cartesian coordinates in the measured image; $c_0, c_{mn}$, s and t are fit-coefficients; and w is a window function. In an embodiment, the target structure is a composite target structure including a plurality of component structures and the combination fit function includes a respective fit function for each of the component structures. In an embodiment, the property is selected from the group consisting of: overlay, focus, dose, CD and asymmetry. In an embodiment, determining a value of at least one coefficient is performed using a non-linear optimization algorithm.

In an embodiment, there is provided a computer program product comprising machine-readable instructions for causing a processor to perform steps of a method of measuring a property of a lithographic process, using measured image of a target structure that has been formed by the lithographic process on a substrate, wherein the image of the target structure has been obtained using an imaging system that selects a predetermined portion of radiation diffracted by the target structure under predetermined illumination conditions; the instructions causing the processor to: identify one or more regions of interest in the measured image; and determine a value of at least one coefficient of a combination fit function using pixel values of the one or more regions of interest, wherein the value of the coefficient is indicative of the property.

In an embodiment, there is provided a lithographic system comprising: a lithographic apparatus comprising: an illumination optical system arranged to illuminate a pattern; a projection optical system arranged to project an image of the pattern onto a substrate; and an inspection apparatus as described herein, wherein the lithographic apparatus is arranged to use the measurement results from the inspection apparatus in applying the pattern to further substrates.

In an embodiment, there is provided a method of manufacturing devices wherein a device pattern is applied to a series of substrates using a lithographic process, the method including measuring at least one composite target structure formed as part of or beside the device pattern on at least one of the substrates using a method as described herein and controlling the lithographic process for later substrates in accordance with the result of the measuring.

An embodiment may include a computer program containing one or more sequences of machine-readable instructions describing a methods of measuring targets on a substrate and/or analyzing measurements to obtain information about a lithographic process. This computer program may be executed for example within unit PU in the apparatus of FIG. 3 and/or the control unit LACU of FIG. 2. There may also be provided a data storage medium (e.g., semiconductor memory, magnetic or optical disk) having such a computer program stored therein. Where an existing metrology apparatus, for example of the type shown in FIG. 3, is already in production and/or in use, the invention can be implemented by the provision of updated computer program products for causing a processor to perform the modified step S6 and so calculate overlay error with improved accuracy. The program may optionally be arranged to control the optical system, substrate support and the like to perform the steps S2-S5 for measurement of asymmetry on a suitable plurality of target structures.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of determining a property of a lithographic process, using a target structure that has been formed by the lithographic process on a substrate, the method comprising:
    forming an image of the target structure using an imaging system of a metrology apparatus that selects a certain portion of radiation diffracted by the target structure under certain illumination conditions;
    measuring the image of the target structure;
    identifying a region of interest in the measured image; and
    determining a value of at least one coefficient of a combination fit function using pixel values of the region of interest,
    wherein the value of the coefficient is indicative of the property of the lithographic process, and
    wherein the combination fit function has at least one fixed coefficient based on a characteristic or parameter (i) of the target structure, (ii) of the metrology apparatus, (iii) of the illumination of the target structure, the forming the image and/or the measuring the image, and/or (iv) of the lithographic process.

2. A method as claimed in claim 1, wherein the combination fit function includes an imaging term representing imaging effects of the imaging system.

3. A method as claimed in claim 2, wherein the imaging term is based on a transfer function of the imaging system.

4. A method as claimed in claim 3, wherein the imaging system includes an aperture and the imaging term is based on a transform of the aperture.

5. A method as claimed in claim 4, wherein the imaging term includes a jinc function.

6. A method as claimed in claim 3, wherein the target structure has an outline that has a plurality of edges and the combination fit function includes a respective imaging term for each of the edges.

7. A method as claimed in claim 1, wherein the combination fit function includes a periodic function representing a disturbance.

8. A method as claimed in claim 1, wherein the combination fit function includes a target term representing an ideal image of the target structure; and the coefficient is a coefficient of the target term.

9. A method as claimed in claim 8, wherein the target term is a constant function and the coefficient is the value of the constant function.

10. A method as claimed in claim 1, wherein the combination fit function includes a window function.

11. A method according to claim 1, wherein determining a value of at least one coefficient is performed using a non-linear optimization algorithm.

12. An inspection apparatus for measuring a property of a lithographic process using a target structure that has been formed by the lithographic process on a substrate, the apparatus comprising:
    a support for the substrate having the target structure formed thereon;
    an illumination system configured to illuminate the target structure under certain illumination conditions;
    an imaging system configured to form an image of the target structure using a certain portion of radiation diffracted by the target structure under the illumination conditions;
    a measuring system configured to measure the image; and
    a processor arranged to identify a region of interest in the detected image and to determine a value of at least one coefficient of a combination fit function using pixel values of the region of interest,
    wherein the value of the coefficient is indicative of the property, and
    wherein the combination fit function has at least one fixed coefficient based on a characteristic or parameter (i) of the target structure, (ii) of the inspection apparatus, (iii) of the illumination of the target structure, the forming the image and/or the measuring the image, and/or (iv) of the lithographic process.

13. The apparatus as claimed in claim 12, wherein the combination fit function includes an imaging term representing imaging effects of the imaging system.

14. The apparatus as claimed in claim 12, wherein the combination fit function includes a periodic function representing a disturbance.

15. The apparatus as claimed in claim 12, wherein the combination fit function includes a target term representing an ideal image of the target structure; and the coefficient is a coefficient of the target term.

16. The apparatus as claimed in claim 12, wherein the combination fit function further includes a window function.

17. The apparatus according to claim 12, wherein the processor is configured to determine a value of at least one coefficient using a non-linear optimization algorithm.

18. A non-transitory computer program product comprising machine-readable instructions for causing a processor to determine a property of a lithographic process, using a measured image of a target structure that has been formed by the lithographic process on a substrate, wherein the image of the target structure has been obtained using an imaging system of a metrology apparatus that selects a certain portion of radiation diffracted by the target structure under certain illumination conditions; the instructions causing the processor to:

identify a region of interest in the measured image; and determine a value of at least one coefficient of a combination fit function using pixel values of the region of interest, wherein the value of the coefficient is indicative of the property of the lithographic process, and wherein the combination fit function has at least one fixed coefficient based on a characteristic or parameter (i) of the target structure, (ii) of the metrology apparatus, (iii) of the illumination of the target structure, the forming the image and/or the measuring the image, and/or (iv) of the lithographic process.

19. A lithographic system comprising:

a lithographic apparatus comprising:

an illumination optical system arranged to illuminate a pattern;

a projection optical system arranged to project an image of the pattern onto a substrate; and an inspection apparatus according to claim 12, wherein the lithographic apparatus is arranged to use the measurement results from the inspection apparatus in applying the pattern to further substrates.

20. A method of manufacturing devices wherein a device pattern is applied to a series of substrates using a lithographic process, the method including measuring at least one target structure formed as part of or beside the device pattern on at least one of the substrates using a method as claimed in claim 1 and controlling the lithographic process for later substrates in accordance with the result of the measuring.

* * * * *